(12) United States Patent
Farber

(10) Patent No.: US 11,903,962 B1
(45) Date of Patent: Feb. 20, 2024

(54) ISOXAZOLINE COMPLEXES AND COMPOSITIONS THEREOF

(71) Applicant: Michael Farber, Livingston, NJ (US)

(72) Inventor: Michael Farber, Livingston, NJ (US)

( * ) Notice: Subject to any disclaimer, the term of this patent is extended or adjusted under 35 U.S.C. 154(b) by 0 days.

(21) Appl. No.: 18/212,233

(22) Filed: Jun. 21, 2023

Related U.S. Application Data

(63) Continuation-in-part of application No. 18/144,220, filed on May 7, 2023.

(51) Int. Cl.
| | |
|---|---|
| *A61K 31/724* | (2006.01) |
| *A61K 9/00* | (2006.01) |
| *A61P 33/14* | (2006.01) |
| *A61K 31/42* | (2006.01) |

(52) U.S. Cl.
CPC ......... *A61K 31/724* (2013.01); *A61K 9/0056* (2013.01); *A61K 31/42* (2013.01); *A61P 33/14* (2018.01)

(58) Field of Classification Search
CPC .... A61K 31/724; A61K 9/0056; A61K 31/42; A61K 33/14
See application file for complete search history.

(56) References Cited

U.S. PATENT DOCUMENTS

| | | |
|---|---|---|
| 9,907,859 B2 | 3/2018 | Tyavanagimatt et al. |
| 10,864,282 B2 | 12/2020 | Tyavanagimatt et al. |

FOREIGN PATENT DOCUMENTS

| | | | | |
|---|---|---|---|---|
| JP | 2020189891 A | * | 11/2020 | ............ A01N 37/46 |
| WO | WO-2016073347 A1 | * | 5/2016 | ........... A61K 31/403 |
| WO | WO-2016124966 A1 | * | 8/2016 | ............ A61K 47/40 |

OTHER PUBLICATIONS

English Translation of Yasumasa JP 2020 189891 (A) by Espacenet—Nov. 26, 2020 (602 pages) (Year: 2020).*
European Medicines Agency—European public MRL assessment report (EPMAR) Feb. 15, 2017 (12 pages) (Year: 2017).*
Zhou et al., "Current review of isoxazoline ectoparasiticides used in veterinary medicine" J Vet Pharmacol Therap. 2022;45:1-15 (Year: 2022).*

\* cited by examiner

*Primary Examiner* — Aradhana Sasan
(74) *Attorney, Agent, or Firm* — Michael J. Feigin, Esq.; Feigin and Fridman LLC

(57) ABSTRACT

A pharmaceutical composition comprising an isoxazoline compound complexed with a cyclodextrin such as hydroxypropyl-cyclodextrin and combined in a dry (anhydrous) composition with polypowder. The composition can be a mixture of isomers, an enriched mixture of a specific enantiomer or a single enantiomer.

19 Claims, No Drawings

ISOXAZOLINE COMPLEXES AND COMPOSITIONS THEREOF

FIELD OF THE INVENTION

The invention relates to the field of pharmaceutical compositions containing isoxazoline compounds for use in animals or poultry.

BACKGROUND

There are several commercial forms of fluralaner which has a chemical formula of 4-[(5RS)-5-(3,5-Dichlorophenyl)-4,5-dihydro-5-(trifluoromethyl)-1,2-oxazol-3-yl]-N-[2-oxo-2-(2,2,2-trifluoroethylamino)ethyl]-o-toluamide. Fluralaner inhibits γ-aminobutyric acid (GABA)-gated chloride channels (GABA receptors) and L-glutamate-gated chloride channels (GluCls).

Fluralaner and afoxolaner belong to a class of compounds called isoxazolines (a class of five-membered heterocyclic chemical compounds having one atom each of oxygen and nitrogen which are located adjacent to one another). Fluralaner is a hydrophobic compound which has been shown in various compositions to undergo degradation by water within about 48 hours at room temperature. Therefore, any commercial compositions with a long shelf life must be anhydrous in nature and their components must not interact negatively with fluralaner or other isoxazolines or be hygroscopic in nature within the appropriate packaging.

Fluralaner is found in anhydrous hard chewable tablets for dogs as well as solvent based with acetone transdermal drops for dogs and cats either alone or combined with macrocyclic lactones. In the prior art the use of various organic solvents such as diacetylacetamide, n-methylpyrrolidone or pyrrolidone enhances uptake of fluralaner in chewables for dogs.

The water in the drinking water supply system in the pigsty or house is subject to the principles of laminar flow through pipes and coils and is subjected to so-called "tangential" forces that will affect the flow rate. In such a complex piping system, there are significant risks to segregation or sedimentation of the drug when using water-insoluble compounds. The effectiveness of the drug through the drinking water supply system as a whole largely depends on the quality of the composition (and its stability in the drinking water supply system) and the taste of the preparation.

A suitable composition should ensure maximum availability of the active ingredient, minimal or no segregation and precipitation of the active substance in the drinking water supply system. It is further ideal to have accurate dosing and even distribution of the active ingredient in drinking water, and guaranteed stability of the active ingredient in the composition itself and after dilution to the target concentration in medicinal drinking water. Such pharmaceutical compositions are envisioned in the current invention which are devoid of any organic solvents.

There exists a need for a delivery system of fluralaner which would provide better water solubility, stability, and taste which is capable of being used in a single form in various compositions whether oral or injectable or transdermal for cats, dogs, poultry, and swine. Ideally, the fluralaner should be combinable synergistically with other components such as macrocyclic lactones or their complexes.

SUMMARY

It has now been surprisingly discovered that a combination of fluralaner (a trifluoro compound) in a hydroxypropyl beta cyclodextrin complex combined in a dry form with an anhydrous polypowder (poly80 adsorbed to hydroxypropyl beta cyclodextrin (hpbcd)) has a water solubility of 20. to 30 mg/ml (where "mg" is milligram" and "ml" is "millimeter") wherein the complex itself has a water solubility of less than 20 mg/ml. In a first test an unexpected result with enhanced solubility of the fluralaner complex with polypowder has been found with 1% fluralaner in water at 0.5 mg/kg (where "kg" is kilogram) in poultry. Further tests have since been conducted as described in the detailed description below.

Similar trifluoro compounds, such as tecovirimat, exhibit fairly high solubility when complexed with hpbcd (>10 mg/ml) but show no enhancement when their complexes are combined with polysorbate 80. In fact, over the range of temperatures from 4 C to 40 C (where "C" is "Celsius") there was a decrease in the solubility of the tecovirimat complex when combined with polysorbate 80 except at 4 C where polysorbate 80 only very slightly enhanced complex solubility.

In the temperature range solubility was decreased with addition of polysorbate 80 compared to tecorivimat complex alone. We have surprisingly found that combining a fluralaner hpbcd complex with an anhydrous polysorbate 80 powder that has long shelf life results in a marked improvement in complex solubility over the temperature range 4 C to 40 C wherein the solubility of the complex is itself less than 20 mg/ml of fluralaner. However, when combined with the polypowder the solubility is enhanced from 20 to 30 mg/ml and dissolution is immediate while the anhydrous powder mixture has long shelf life stability.

The combined powder can thus be fabricated into all the desirable forms such as anhydrous, soft chewable, anhydrous hard chewables, and water solutions (for use with metered water delivery systems or as micro pellets for feed inclusion or powder as a mix for feed) or even immediately injectable forms.

Thus, there are numerous advantages of the composition compared to the prior art which include long shelf life, improved taste masking of the isoxazoline components, instant dissolution, and synergistic combinations with macrocyclic lactone complexes for combined therapeutics to dogs, cats, swine and other husbandry animals.

The invention envisions the combination with macrocyclic lactones or preferably their cyclodextrin complexes for prolonged shelf life and enhanced absorption as well as trio combinations with drugs such as pyrantel or praziquantel and numerous other drugs currently used in animal husbandry for treatment of endo and ectoparasites. More advantageously the use of polypowder with the fluralaner complex, in embodiments of the disclosed technology, can be combined with various other cyclodextrin complexes allowing for greater absorbion and/or solubilization with medicaments used for endo or ectoparasites in husbandry animals.

In a method of treating an animal parasitic infection using a shelf stable anhydrous pharmaceutical composition an isoxazoline cyclodextrin complex maximally soluble to less than 20 mg/ml in water is combined with polypowder, such as a polysorbate adsorbed onto 2 hydroxypropyl beta cyclodextrin in an anhydrous form. The polypowder, before being combined with the isoxazoline has a shelf life of at least 2 years. The polypowder is combined with the isoxazoline cyclodextrin complex giving a solubility of from 20 mg to 30 mg/ml of isoxazaline in water and formed into a dry anhydrous medicament with a shelf life of at least 2 years. The medicament is administrable with medicinal effect through water or feed orally ingested by an animal.

Described another way, an orally administrable medicament which treats animal parasite infections and which is adapted to be safely ingested by an animal has a polypowder has a polysorbate adsorbed onto 2-hydroxypropyl-beta-cyclodextrin in an anhydrous form having a shelf life of at least 2 years. A shelf stable anhydrous pharmaceutical composition with a combination of an isoxazoline cyclodextrin complex, maximally soluble to between 20 mgml to 30 mg/ml of isoxazoline inclusive, in water is thus created wherein a combination of said isoxazoline cyclodextrin complex with the adsorbed polysorbate forms a dry anhydrous medicament with a shelf life of at least 2 years.

The polypowder can be any polysorbate adsorbed onto a cyclodextrin under anhydrous conditions. The isoxazoline cyclodextrin complex can be a fluralaner cyclodextrin complex administered in water or feed at 0.5 mg/kg of bodyweight of poultry being treated. The said fluralaner cyclodextrin complex can be administered twice in a period between 7 to 14 days. The isoxazoline complex and polypowder mixture is a fluralaner complex and polypowder mixture administered in hard or soft anhydrous chews at a rate of 2 to 4 mg/kg per month in a feline or canine, in some embodiments of the disclosed technology.

The isoxazoline complex and polypowder mixture are combined synergistically with cyclodextrin complexes of macrocyclic lactones increasing solubility and bioavailability and improving taste parameters of the medicants in some embodiments of the disclosed technology.

Pyrantel pamoate is combined, in some embodiments of the disclosed technology, with a medicament, wherein the combination provides broad spectrum antiparasitic efficiency in an anhydrous shelf stable chewable form. The isoxazoline can alternatively or additionally be complexed with a cyclodextrin in a stoichiometric ratio of 1:1 or 1:2. The cyclodextrin can be 2-hydroxypropyl-beta-cyclodextrin.

The isoxazoline cyclodextrin complex can be a fluralaner cyclodextrin complex that has a limited water solubility less than 2 mg/ml that is enhanced by combination with a polysorbate polypowder. The improved water solubility of the fluralaner complex combined with polysorbate polypowder is, in some embodiments, from 20 mg/ml to 30 mg/ml in water, inclusive.

The animal which receives the medicament can be a feline, canine, bovine or porcine animal. The animal parasitic infestation can be a tick or lice infestation and the animal may suffer an infestation which is one or both of endoparasitic and ectoparasitic in nature. The animal parasitic infestation can be a tick infestation of one of a *Dermanyssus* or *Ornithonyssus* species.

DETAILED DESCRIPTION

The present invention relates to the use of a pharmaceutical composition comprising an isoxazoline compound complexed with a cyclodextrin such as hydroxy-propyl-cyclodextrin and combined in a dry (anhydrous) composition with polypowder. The composition can be a mixture of isomers, an enriched mixture of a specific enantiomer or a single enantiomer.

The isoxazoline compound for use in the present invention may be described by the formula (hereinafter, "the formula"):

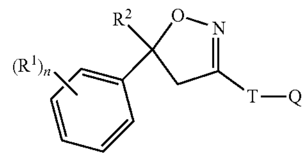

$R^1$=halogen, $CF_3$, $OCF_3$, CN,

N=integer from 0 to 3, preferably 1, 2 or 3, $R^2$=$C_1$-$C_3$-halogenated, preferably $CF_3$ or $CF_2Cl$, T=5- or 6-membered ring, which is optionally substituted by one or more radicals Y, Y=methyl, halomethyl, halogen, CN, $NO_2$, $NH_2$—C═S, or two adjacent radical Y together form a chain, mainly a three- or four-membered chain;

Q=X—$NR^3R^4$ or 5-membered N-heteroaryl ring, which is optionally substituted by one or more radicals;

X=$CH_2$, $CH(CH_3)$, CH(CN), CO, CS, $R^3$, halogen (N, N-dimethylamino)-carbonylmethyl, propylaminocarbonylmethyl, cyclopropylaminocarbonylmethyl, propenylaminocarbonylmethyl, halogenethylaminocarbonylcyclopropyl 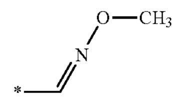 $R^3$-1

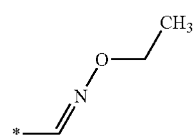

$R^3$-2

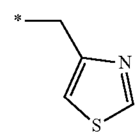

$R^3$-3

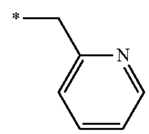

$R^3$-4

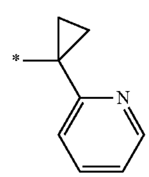

$R^3$-5

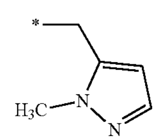

$R^3$-6

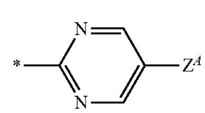

$R^3$-7

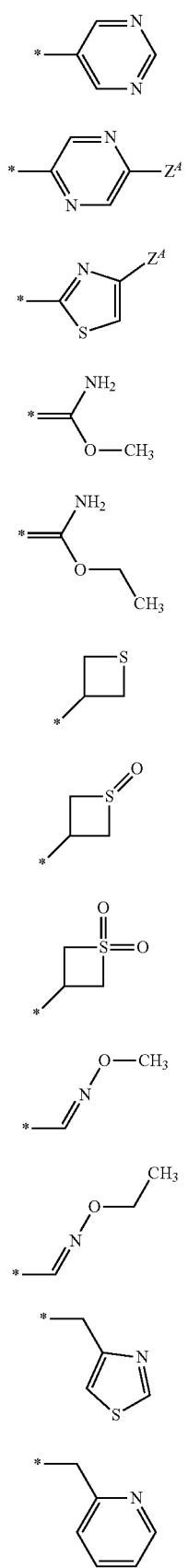
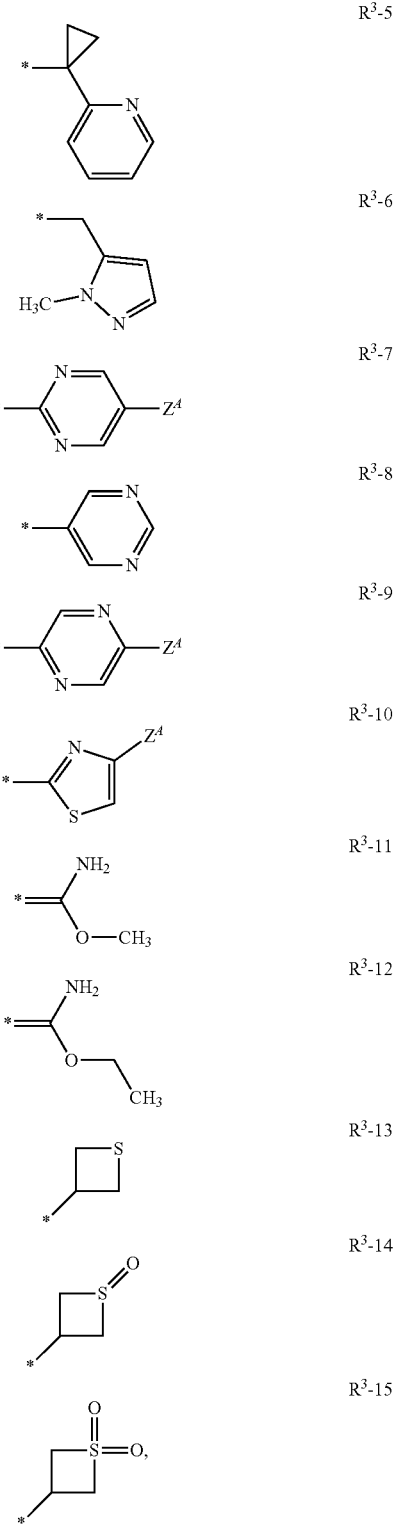

where $Z^A$=hydrogen, halogen, cyano, halomethyl (CF$_3$
R$^4$=hydrogen, ethyl, methoxymethyl, galogenmetoksimetil, ethoxymethyl, galogenetoksimetil, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, etilaminokarboniletil, dimethoxyethyl, propinilaminokarbonilmetil, galogenetilaminokarbonilmetil, cyanomethylaminocarbonylmethyl or galogenetilaminokarboniletil;

or R³ and R⁴ together form a substituent selected from the group consisting of:

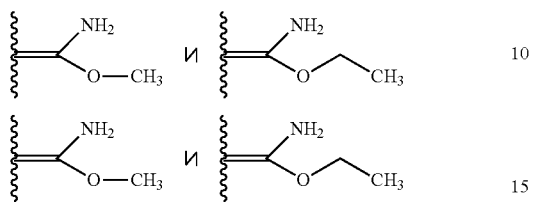

In the cyclodextrin complex, which can be hydroxypropyl-beta-cyclodextrin mixed with a polypowder polysorbate, the complex is adsorbed onto hpbcd to form a medicament for administration through dissolution in drinking water for the prevention or treatment of animal parasitic invasions. The medicament, being anhydrous and having a long shelf-life in a dried form, can then be placed into drinking water or feed for animals. As such, treatment or prevention of parasitic invasions of animals can be accomplished. When placed in feed, a micropellet form can be used. In other embodiments a hard chewable (rigid when pinched lightly) or soft chewable (squeezes together when pinched lightly) medicinal treats for cats or dogs can be used.

In addition, it has been found that such compositions can be used to prepare medicinal water, which is stable for a period of time allowing distribution to the housed animals (no less than 24 hours) and can be evenly distributed in the system to ensure the introduction of an effective amount of isoxazoline compounds to animals through the drinking water supply system.

In the formula above, T can be selected from:

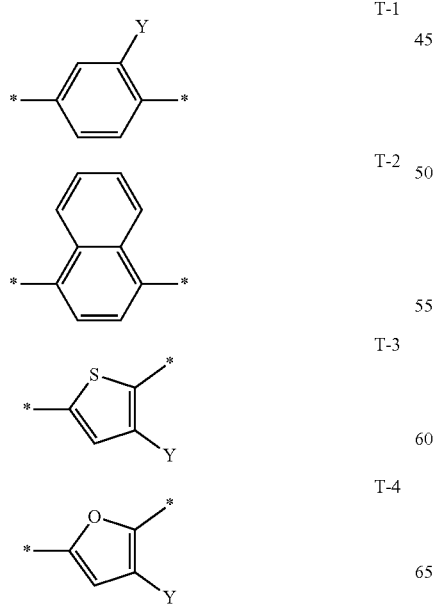

T-1

T-2

T-3

T-4

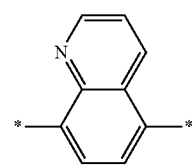

T-5

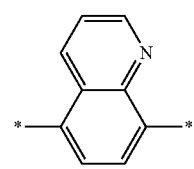

T-6

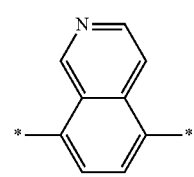

T-7

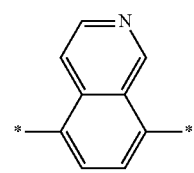

T-8

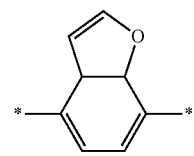

T-9

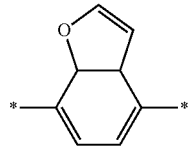

T-10

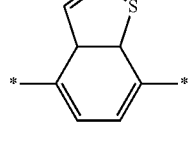

T-11

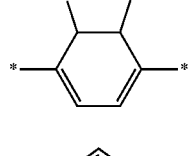

T-12

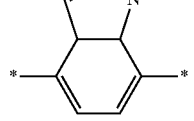

T-13

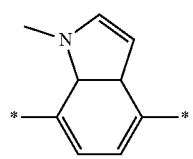
T-14
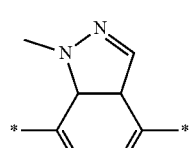
T-15
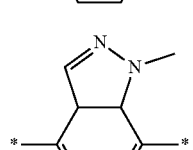
T-16
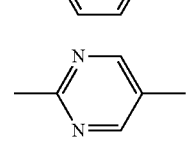
T-17
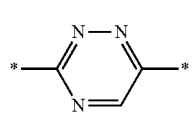
T-18
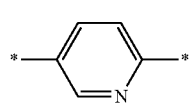
T-19
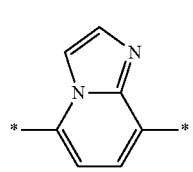
T-20
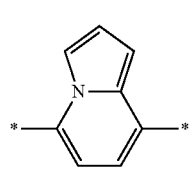
T-21
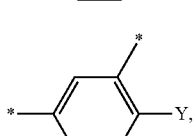
T-22
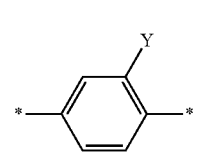
T-1
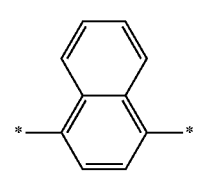
T-2
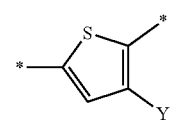
T-3
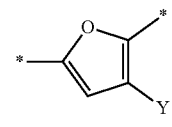
T-4
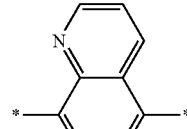
T-5
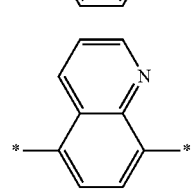
T-6
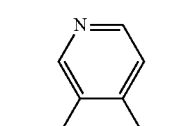
T-7
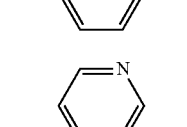
T-8
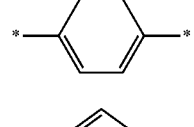
T-9
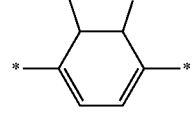
T-10
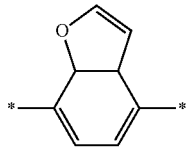
T-11
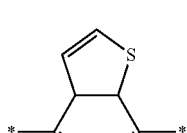
T-12
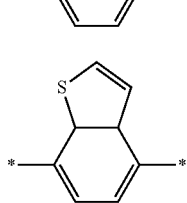

-continued
T-13 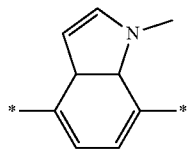
T-14 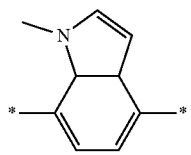
T-15 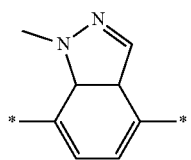
T-16 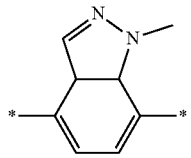
T-17 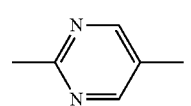
T-18 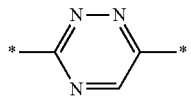
T-19 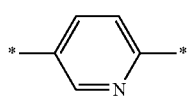
T-20 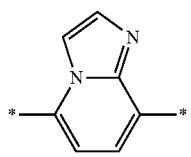
T-21 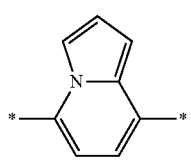
T-22 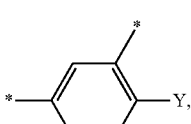
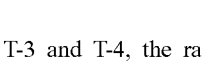
wherein in T-1, T-3 and T-4, the radical Y is hydrogen, halogen, methyl, halomethyl, ethyl, halogen ethyl.
In the formula above, Q can be selected from:
Q-1 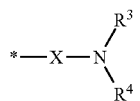
Q-2 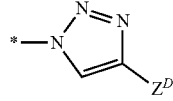
Q-3 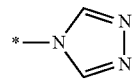
Q-4 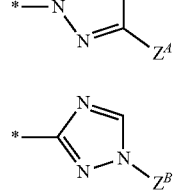
Q-5 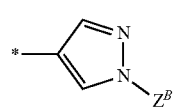
Q-6 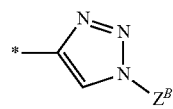
Q-7 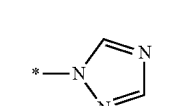
Q-8 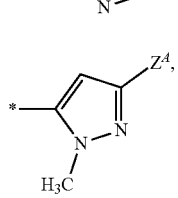
Q-9 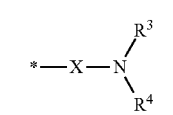
Q-1 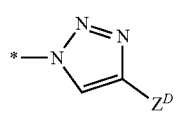
Q-2 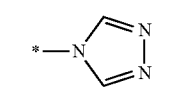
Q-3 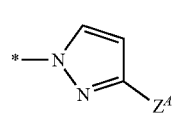
Q-4 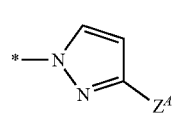

where $R^3$, $R^4$, X and $Z^A$ have the above values.

$Z^b$ =

$Z^D$=

Isoxazoline compounds of the formula for use in the present invention are:

$(R^{one})_nR^2R^3R^{four}$TYQZX3-Cl, 5ClCF$_3$CH$_2$CF$_3$HT-2-Q-1-C(O)$_3$—Cl, 5ClCF$_3$CH$_2$CH$_3$HT-2-Q-1-C(O)$_3$—Cl, 5ClCF$_3$CH$_2$CH$_2$OCH$_3$HT-2-Q-1-C(O)$_3$—Cl, 5ClCF$_3$CH$_2$C(O)NHCH$_2$CF$_3$HT-2-Q-1-C(O)$_3$—Cl, 5ClCF$_3$CH$_2$C(O)NHCH$_2$CH$_3$HT-2-Q-1-C(O)$_3$—CF$_3$, 5-CF$_3$CF$_3$CH$_2$C(O)NHCH$_2$CF$_3$HT-2-Q-1-C(O)$_3$—CF$_3$, 5-CF$_3$CF$_3$CH$_2$C(O)NHCH$_2$CH$_3$HT-2-Q-1-C(O)$_3$-CF$_3$, 5-ClCF$_3$CH$_2$C(O)NHCH$_2$CF$_3$HT-2-Q-1-C(O)$_3$—CF$_3$, 5-ClCF$_3$CH$_2$C(O)NHCH$_2$CH$_3$HT-2-Q-1-C(O)$_3$—Cl, 5ClCF$_3$-T-2-Q-6Z$^B$-73-Cl, 5ClCF$_3$-T-2-Q-7Z$^B$-7 3-Cl, 5ClCF$_3$-T-2-Q-5Z$^B$-73-Cl, 5ClCF$_3$-T-2-Q-2Z$^D$-13-Cl, 5ClCF$_3$CH$_2$C(O)NHCH$_2$CF$_3$HT-3CH$_3$Q-1-C(O)$_3$—Cl, 5ClCF$_3$CH$_2$C(O)NHCH$_2$CCHT-3CH$_3$Q-1-C(O)$_3$—Cl, 5ClCF$_3$CH$_2$C(O)NHCH$_2$CNHT-3CH$_3$Q-1-C(O)$_3$—Cl, 5ClCF$_3$CH$_2$C(O)NHCH$_2$CH$_3$HT-3CH$_3$Q-1-C(O)$_3$—CF$_3$, 5-CF$_3$CF$_3$CH$_2$C(O)NHCH$_2$CF$_3$HT-3CH$_3$Q-1-C(O)$_3$—CF$_3$, 5-CF$_3$CF$_3$CH$_2$C(O)NHCH$_2$CH$_3$HT-3CH$_3$Q-1-C(O)$_3$—Cl, 4-Cl, 5-ClCF$_3$CH$_2$C(O) NHCH$_2$CF$_3$HT-3CH$_3$Q-1-C(O)$_3$—Cl, 4-Cl, 5-ClCF$_3$CH$_2$C(O) NHCH$_2$CH$_3$H T-3CH$_3$Q-1-C(O)$_3$—Cl, 4-F, 5-ClCF$_3$CH$_2$C(O)NHCH$_2$CF$_3$HT-3CH$_3$Q-1-C(O) 3-Cl, 4-F, 5-ClCF$_3$CH$_2$C(O)NHCH$_2$CH$_3$HT-3CH$_3$Q-1-C(O)$_3$—Cl, 5-ClCF3CH$_2$C(O)NHCH$_2$CF$_3$HT-20-Q-1-C(O)$_3$—Cl, 5-ClCF$_3$CH$_2$C(O)NHCH$_2$CH3 HT-20-Q-1-C(O)$_3$—CF$_3$, 5-CF$_3$CF$_3$CH$_2$C(O)NHCH$_2$CF$_3$CH$_3$T-20-Q-1-C(O)$_3$—CF$_3$, 5-CF$_3$CF$_3$CH$_2$C(O)NHCH$_2$CH$_3$CH$_3$T-20-Q-1-C(O)$_3$—CF$_3$, 5-CF$_3$CF$_3$CH$_2$C(O) NHCH$_2$CF$_3$HT-20-Q-1-C(O)$_3$—CF$_3$, 5-CF$_3$CF$_3$CH$_2$C (O) NHCH$_2$CH$_3$HT-20-Q-1-C(O)$_3$—CF$_3$, 5-CF$_3$ CF$_3$CH$_2$C(O)NHCH$_2$CF$_3$H T-21-Q-1-C(O)$_3$—CF$_3$, 5-CF$_3$CF$_3$CH$_2$C(O)NHCH$_2$CH$_3$HT-21-Q-1-C(O)$_3$-Cl, 5-ClCF$_3$CH$_2$C(O)NHCH$_2$CF$_3$HT-21-Q-1-C(O)$_3$—Cl, 5-ClCF$_3$CH$_2$C(O) NHCH$_2$CH$_3$HT-21-Q-1-C(O)$_3$—Cl, 5-ClCF$_3$CH$_2$CH$_2$SCH$_3$HT-21-Q-1-C(O)$_3$—Cl, 4-Cl, 5-ClCF$_3$C(O)CH$_3$HT-22FQ-1-CH$_2$3-Cl, 4-Cl, 5-ClCF$_3$C(O) CH(CH$_3$)$_2$HT-22FQ-1-CH$_2$3-Cl, 4-Cl, 5-ClCF$_3$C(O)-cyclopropyl HT-22F Q-1-CH$_2$3-Cl, 4-F, 5-ClCF$_3$C(O)CH$_3$HT-22F Q-1-CH$_2$3-Cl, 4-Cl, 5-ClCF$_3$C(O) CH$_2$CH$_3$HT-22FQ-1-CH$_2$3-Cl, 4-F, 5-ClCF$_3$C(O)CH$_3$HT-22Cl Q-1-CH$_2$3-Cl, 5-ClCF$_3$ CH$_2$C(O)NHCH$_2$ CF$_3$HT-1CH$_3$Q-1-C(O)$_3$—Cl, 5-ClCF$_3$CH$_2$C(O)NHCH$_2$CH$_3$HT-1CH$_3$Q-1-C(O)$_3$—Cl, 5-ClCF$_3$R 3-1 (Z)HT-1CH$_3$Q-1-C(O)$_3$—Cl, 5-ClCF$_3$R 3-1 (E)HT-1CH$_3$Q-1-C(O)

Isoxazoline compounds for use in the present invention include:

$(R^{one})_nR^2R^3R^{four}$TYQZX3-Cl, 5ClCF$_3$CH$_2$CF$_3$HT-2-Q-1-C(O)$_3$—Cl, 5ClCF$_3$CH$_2$CH$_3$HT-2-Q-1-C(O)$_3$—Cl, 5ClCF$_3$CH$_2$CH$_2$OCH$_3$HT-2-Q-1-C(O)$_3$—Cl, 5ClCF$_3$CH$_2$C(O)NHCH$_2$CF$_3$HT-2-Q-1-C(O)$_3$—CF$_3$, 5-CF$_3$ CF$_3$CH$_2$C(O)NHCH$_2$CF$_3$HT-2-Q-1-C(O)$_3$—CF$_3$, 5-ClCF$_3$CH$_2$C(O)NHCH$_2$CF 3 HT-2-Q-1-C(O)$_3$—Cl, 5ClCF$_3$-T-2-Q-6Z$^B$-7 3-Cl, 5ClCF$_3$-T-2-Q-7Z$^B$-7 3-Cl, 5ClCF$_3$-T-2-Q-5Z$^B$-7 3-Cl, 5ClCF$_3$-T-2-Q-2Z$^D$-13-Cl, 5ClCF$_3$CH$_2$C(O)NHCH$_2$CF$_3$HT-3CH$_3$Q-1-C(O)$_3$—Cl, 5ClCF$_3$CH$_2$C(O)NHCH$_2$CC HT-3CH$_3$Q-1-

C(O)₃—Cl, 5ClCF₃CH₂C(O)NHCH₂CN HT-3CH₃Q-1-C(O)₃-CF₃, 5-CF₃CF₃CH₂C(O)NHCH₂CF₃HT-3CH₃Q-1-C(O)₃—Cl, 4-Cl, 5-Cl CF₃CH₂C(O)NHCH₂CF₃HT-3CH₃Q-1-C(O)₃—Cl, 4-F, 5-ClCF₃CH₂C(O) NHCH₂CF₃HT-3CH₃Q-1-C(O)₃—Cl, 5-ClCF₃CH₂C(O)NHCH₂CF₃HT-20-Q-1-C(O)₃—CF₃, 5-CF₃CF₃CH₂C(O)NHCH₂CF₃CH₃T-20-Q-1-C(O)₃-CF₃, 5-CF₃CF₃CH₂C(O)NHCH₂CF₃HT-20-Q-1-C(O)₃—CF₃, 5-CF₃CF₃CH₂C(O)NHCH₂CF₃HT-21-Q-1-C(O)₃—Cl, 5-ClCF₃CH₂C(O)NHCH₂CF₃HT-21-Q-1-C(O)₃—Cl, 5-ClCF₃CH₂CH₂SCH₃HT-21-Q-1-C(O)₃—Cl, 4-Cl, 5-ClCF₃C(O)CH₃HT-22FQ-1-CH₂3-Cl, 4-Cl, 5-ClCF₃C(O)CH(CH₃)₂HT-22FQ-1-CH₂3-Cl, 4-Cl, 5-ClCF₃C(O)-cyclopropyl HT-22FQ-1-CH₂3-Cl, 4-F, 5-ClCF₃C(O)CH₃HT-22FQ-1-CH₂3-Cl, 4-Cl, 5-ClCF₃C(O)CH₂CH₃HT-22FQ-1-CH₂3-Cl, 4-F, 5-ClCF₃C(O)CH₃HT-22ClQ-1-CH₂3-Cl, 5-Cl CF₃CH₂C(O)NHCH₂CF₃HT-1CH₃Q-1-C(O)₃—Cl, 5-ClCF₃R 3-1(Z)HT-1CH₃Q-1-C(O)₃—Cl, 5-ClCF₃R³-1(E)HT-1CH₃Q-1-C(O)

Another isoxazoline compound for use in the present invention is a second formula (hereinafter, "second formula"):

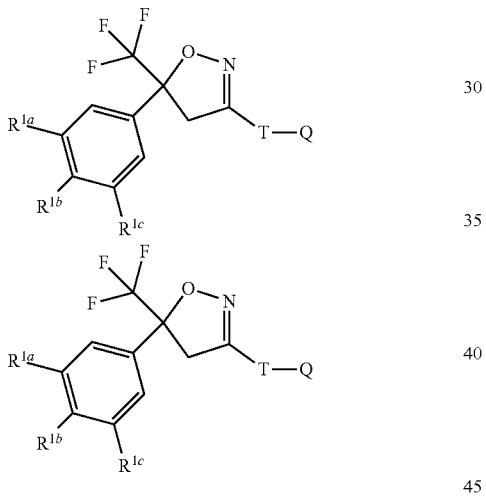

wherein $R^{1a}$, $R^{1b}$, $R^{1c}$ independently of one another represent hydrogen, Cl or CF₃, preferably $R^{1a}$ and $R^{1c}$ represent Cl or CF₃, and $R^{1b}$ represents hydrogen, T represents

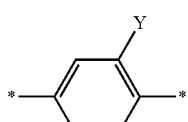  T-1

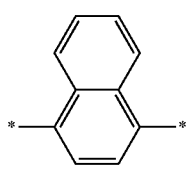  T-2

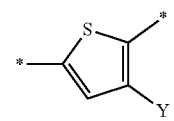  T-3

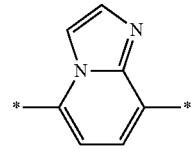  T-20

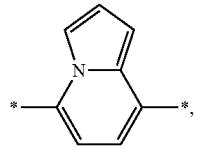  T-21

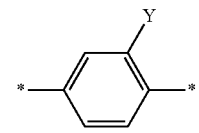  T-1

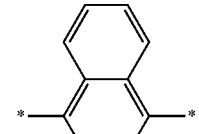  T-2

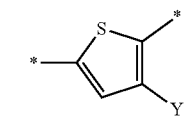  T-3

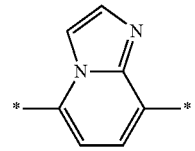  T-20

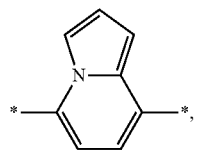  T-21

Where
Y is methyl, bromine, Cl, F, CN or C(S) NH₂, and
Q is as described above.

In another embodiment, in the second formula, $R^3$ is H, and $R^4$ is —CH₂—C(O)—NH—CH₂—CF₃, —CH₂—C(O)—NH—CH₂—CH₃, —CH₂—CH₂—CF₃ or —CH₂—CF₃.

In some embodiments of the disclosed invention the isoxazoline compound is 4-[5-(3,5-dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3—USAN fluralaner).

In some embodiments the isoxazoline compound is (Z)-4-[5-(3,5-dichlorophenyl)-5-trifluoromethyl-4,5-dihydroisoxazol-3-yl]-N-[(methoxyimino)methyl]-2-methylbenzamide (CAS RN 928789-76-8).

In some embodiments the isoxazoline compound is 4-[5-(3,5-dichlorophenyl)-5-(trifluoromethyl)-4H-isoxazol-3-yl]-2-methyl-N-(thietan-3-yl)benzamide (CAS RN 1164267-94-0), which was disclosed in application WO 2009/0080250.

In some embodiments the isoxazoline compound is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN—afoxolaneer), which was disclosed in WO 2007/079162.

In some embodiments the isoxazoline compound is 1-[5'-[(5S)-5-(3,5-dichloro-4-fluorophenyl)-4,5-dihydro-5-(trifluoromethyl)-3-isoxazolyl]spiro [azetidin-3,1'(3'H)-isobenzofuran]-1-yl]-2-(methylsulfonyl) ethanone—(Sarolaner) (CAS RN 1398609-39-6).

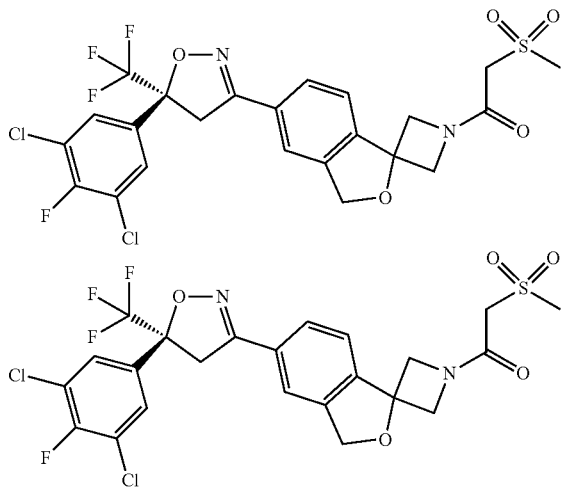

In some embodiments the isoxazoline compound is 5-((5S)-4,5-dihydro-5-(3,4,5-trichlorophenyl)-5-(trifluoromethyl)-3-isoxazolyl)-3-methyl-N-(2-oxo-2-((2,2,2-trifluoroethyl)amino)ethyl)-2-thiophenecarboxamide—(Lotilaner INN) (CAS RN 1369852-71-0).

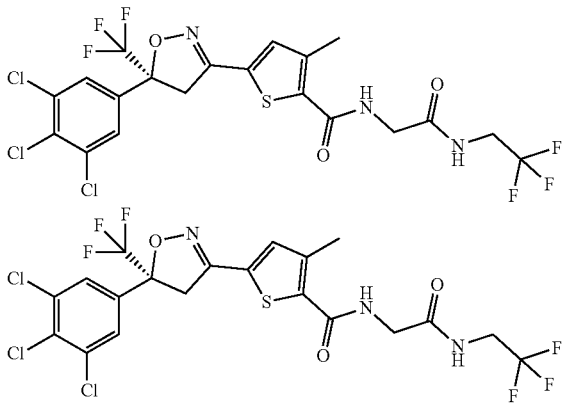

In some embodiments the isoxazoline compound is 5-[5-(3,5-dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophene carboxamide (CAS RN 1231754-09-8), which was disclosed in WO 2010/070068.

Racemic mixtures can be used, for example, equal amounts of the enantiomers of any of the isoxazoline compounds as described above. Furthermore, the method of the present invention includes isoxazoline compounds that are enriched to the enantiomer of the first formula as compared to a racemic mixture. Substantially pure enantiomers of such isoxazoline compounds can also be used with methods described in this disclosure.

In enantiomeric enrichment, one enantiomer is present in greater quantity than the other, and the degree of enrichment can be determined by the expression of enantiomeric excess ("ee"), which is defined as $(2x-1)-100\%$, where x is the mole fraction of the dominant enantiomer in the mixture (for example, ee 20% corresponds to the ratio of enantiomers of 60:40). The compositions for use in the present invention have at least a 50% enantiomeric excess in some embodiments and at least 75% enantiomeric excess in a subset of such embodiments. In other cases 90% to 94% enantiomeric excess of the more active isomer is achieved. Of particular note are enantiomerically pure embodiments of the more active isomer.

The isoxazoline compounds described above may contain additional chiral centers. The method of the invention includes racemic mixtures as well as enriched and substantially pure stereo configurations at these additional chiral centers.

The isoxazoline compound, as described above, in embodiments of the invention, is present in the in an amount from about 0.001 mg/ml to about 30 mg/ml upon dilution of the dry powder in water. A mixture of a isoxazoline with fluralaner in a cyclodextrin complex combined with a polypowder as a dry mixture can immediately (in less than one minute) form a concentrated solution from 20 mg/ml to 30 mg/ml of isoxazoline compound in water, ready for immediate distribution as a solution for animals or poultry to be treated. This solution can be further diluted if necessary.

Compositions according to the present invention have particularly favorable properties, such as long-term stability (two or more years) after storage, favorable taste profiles, and the absence of precipitation of the isoxazoline compounds after diluting such a composition in water or ingestion of the isoxazoline in chewable tablet or powder form.

A polysorbate surfactant (such as a sorbitol ester or poly (hydroxy-1,2-ethanediyl) derivatives) is a water-soluble non-ionic surface-active agent comprising or consisting of esters and esters of alkoxyacids. The esters are derived from six-alcohols, alkylene oxides and fatty acids adding polyoxyethylene chains to hydroxyl sorbitol and hexitol anhydrides (hexitanes and hexides) obtained from sorbitol which then undergo esterification with common fatty acids, such as lauric, palmitic, stearic and oleic acid.

In one embodiment, the polysorbate surfactant is selected from one or more of Tween 20, Tween 40, Tween 60 and Tween 80, also known in the pharmaceutical industry as Polysorbate 20, Polysorbate 40, Polysorbate 60 and Polysorbate 80. Polysorbate 20 (polyoxyethylated sorbitan monolaurate) is a laurate ester; polysorbate 60 (polyoxyethylated sorbitan monostearate) is a mixture of stearate esters and palmitate; and polysorbate 80 (polyoxyethylated sorbitan monooleate) is an oleate ester. Such polysorbate surfactants are commercially available and/or can be obtained by methods known in the art. These polysorbates are adsorbed under anhydrous conditions onto hydroxypropyl beta cyclodextrin to form polypowder which is dry mixed with the isoxazoline cyclodextrin complex forming the highly water soluble dry mix.

In some embodiments the polysorbate surfactant is polysorbate 80 (polyoxyethylene sorbitan monooleate, Tween 80), which has the chemical name polyoxyethylene (20) sorbitan monooleate, and is adsorbed onto 2 hydroxypropyl beta cyclodextrin as an anhydrous flowable compressible powder with long term shelf life.

A preservative is used in some embodiments such as benzyl alcohol, butyl paraben sodium salt, methyl paraben sodium salt, propyl paraben sodium salt, and mixtures thereof. However, given that the shelf life of the medicament is greater than two years, preservatives in such embodiments are typically unnecessary. An antioxidant may be used in some embodiments such as butylated hydroanisole, butylated hydrotoluene, tocopherol, and its derivative as α-tocopherol polyethylene glycol succinate and mixtures thereof. However, given that the shelf life of the medicament is greater than two years, antioxidants in such embodiments are typically unnecessary.

The term "treating" or "treat" or "treatment" is defined as "applying or administering a composition of the invention to an animal that has parasitic invasion to eliminate the parasite or reduce the number of parasites infecting one or more animals".

The parasites eliminated or reduced can be those in the phrases of ovicidal, larvicidal, adults, or a combination thereof. The effect can manifest itself directly, i.e. killing parasites either immediately or after some time has passed, for example, when molting occurs, or destroying their eggs, or indirectly, for example, by reducing the number of eggs laid and/or the rate of hatching from eggs.

"Prevention" or "prevention" is defined as "stopping a future event from happening which would otherwise happen" which, in this invention can be preventing of a new infection of animals with parasites by killing adult parasites and/or any developmental/larval stage that can infect the host before the infection of the host or immediately after infection of the protected parasites. Such prevention can be by way of by reducing the number of eggs laid and/or the rate of hatching of the eggs.

The term "effective amount" is defined as a dosage or amount of an isoxazoline compound that is required to partially reduce or reduce the number of parasites on an animal and/or in an animal environment, such as a house/structure, and/or inhibit the development of a parasitic infection on an animal in whole or in part. The effective amount, in embodiments of the invention, is determined by observing or detecting the number of parasites either on the animal or in the animal's environment (for example, using a trap) both before and after the introduction of the isoxazoline compound, the introduction of the compound being through drinking water or on/in feed. For example, a target may be to decrease the number of parasites by 5% to substantially 100% after a first treatment and this is measurable by catching and/or counting and/or making educated approximations of the number of parasites in a given location.

Parasitic invasions can be either invasions by ectoparasites or endoparasites. In one embodiment the parasitic invasion that is prevented or treated is an invasion by ectoparasites. Specific examples of ectoparasites include, but are not limited to, fleas (*Ctenocephalides felis*, species *Ctenocephalides*, and the like), ticks (species *Rhipicephalus*, form *Ixodes*, species *Dermacentor*, species *Amblyomma*, species *Haemaphysalis*, species *Boophilus*, and the like), and mites (type *Demodex*, species *Sarcoptes*, species *Otodectes*, species *Cheyletiella*, species *Dermanyssus*, species *Ornithonyssus*, etc., lice (species *Trichodectes*, species *Felicola*, species *Linognathus*, etc.), mosquitoes (species *Aedes*, *Culex* species, *Anopheles* species, etc.) and flies (*Hematobia* species, including *Haematobia irritans*, *Musca* species, *Stomoxys* species, including *Stomoxys calcitrans*, *Dermatobia* species, *Cochliomyiaspecies* and the like oh).

The isoxazoline composition can be used for treatment or prevention of parasitic infections in animals such as pigs, cattle, horses, goats, sheep, dogs, cats, poultry and fish.

The isoxazoline medicament can be administered using systemic administration. "Systemic administration" is defined as "an introduction to a place remote from the place where at least part of the targeted parasites live". Upon systemic administration, at least part of the compound reaches the target parasite through the blood of the recipient animal, other biological fluids (lymphatic fluid) and/or tissues (for example, skin or adipose tissue). The parasite swallows the compound along with the blood of the animal recipient, other body fluids and/or tissues in many cases. The systemic administration can be carried out in several forms, for example, oral, parenteral or topical. When carried out parenterally, this can be intramuscular injection, intravenous injection or subcutaneous injection. The medicament, in some embodiments, is administered orally in a liquid such as through a syringe with a part thereof inserted in a mouth of an animal. Alternatively, oral administration can be carried out through the recipient animal's feed or drinking water. When administered in the drinking water, this may be for the prevention or treatment of invasions of parasitic arthropod animals.

In one embodiment, the pharmaceutical composition may be used to treat or prevent parasitic invasions of animals, especially farm animals (eg, cattle, poultry, and pigs), using isoxazoline compounds, such as fluralaner, through drinking water systems.

The final concentration of the isoxazoline compound in medicinal drinking water depends on the effective amount, body weight of the animal, the animal's water consumption and the treatment period. In general, an effective amount per kg of body weight of animals treated is due to the type of parasitic infection. In one embodiment, the treatment water has a concentration of from 0.002 to 0.2 mg/ml of the isoxazoline compound in a cyclodextrin complex mixed with polypowder.

For some isoxazoline compounds with fluralaner the concentration in medicinal drinking water is calculated to provide the target amount of fluralaner per body weight (MT) of poultry to be treated in the range of from about 0.1 mg to about 2 mg of fluralaner per kilogram of body weight, such as more specifically, 0.5 mg/kg per body weight in a day. Such an amount of compound is placed in the volume of drinking water normally consumed by the poultry to be treated during the treatment period from 2 to 24 hours, preferably from 4 to 8 hours. The pharmaceutical composition can be made available during the treatment period for one animal or at the same time for a group of animals, such as poultry (chickens, turkeys, etc.) and pigs, or for such animals in one room (house) or farm through medicinal drinking water. Chickens kept on an industrial scale, such as laying hens, raising chickens or repair chickens, breeding layers, and growing broiler chickens and breeding birds are all treatable using this method. Other types of poultry, such as, for example, turkeys, geese, ducks, pigeons, quails or pheasants can be treated with the compounds as well.

The frequency of treatment with a pharmaceutical composition through medicinal drinking water depends on the parasite from which the prophylaxis is treated or carried out (and on its biological life cycle) and the production cycle of the host animal undergoing treatment. The pharmaceutical composition of the present invention is administered through medicinal drinking water at least once or twice in the production cycle of the animal host being treated (for example, the laying period in the case of laying hens). By introducing the pharmaceutical composition through medicinal water with this effect, a higher efficacy against parasites can be achieved, since different stages of the life cycle of the parasite can be influenced. Under this scheme of introduction, the parasite population can be reduced to a level that causes only minimal damage to animals and minimal production losses.

For some parasites, not all stages of the parasite can be influenced by a single administration of the pharmaceutical composition through medicinal drinking water because certain stages of the parasite either do not feed on the animal or otherwise. With the introduction of a second dose of the pharmaceutical composition through medicinal drinking water, the parasites that have developed (after the life cycle of the parasites) from non-susceptible stages, or parasite stages that are difficult to influence, such as those that matured from the juvenile parasite stages, can be affected (such as eggs, nymphs or pupae) during this period. In the case of treatment of poultry, the pharmaceutical composition can be administered through medicinal drinking water or feed at an interval of approximately or exactly 7 days or 14 days (depending on the life cycle of the parasite and the production cycle of the host animal) once or twice during the production cycle.

In one embodiment the pharmaceutical composition is administered through medicinal drinking water to treat or prevent tick infestation. Some ticks migrate from birds, rodents, food material, plant material and house dust and can attack and annoy animals and people. There are various categories of mites, including northern chicken mites (*Ornithonyssus sylviarum*), red avian mites (*Dermanyssus gallinae*), glandlings (*Demodex folliculorum*), and scabby mites or pruritus mites (*Sarcoptes* species, *Cheyletiella* species, *Psorioptes* species). A tick infestation by a poultry mite can be that of a *Dermanyssus* species (eg, *D. gallinae*) and/or *Ornithonyssus* species, especially *Ornithonyssus sylviarum*.

In one embodiment, the administration of the pharmaceutical composition through the treated drinking water or feed in accordance with the invention controls the stages of parasitic arthropods, as described above, that are present in the environment of poultry. The stages of parasitic arthropods can be all stages of the life cycle that are known to those skilled in the art, that is, both the juvenile stage (development/larval stage) and the adult insect stage.

In one embodiment, administering the pharmaceutical composition through medicinal drinking water or feed in accordance with the invention fights arthropods in poultry, especially broiler chickens, which, as a rule, do not directly infect animals, but provide harm to animals, such as, for example, dark-brows.

In the complexed product described above which lacks solvents, two groups of six laying hens each were given one dose of 0.5 mg/kg of fluralaner in purified water with chicken feed. The prior art is entitled "Exzolt" which has 10 mg fluralaner per ml of solution for use in drinking water for chickens with α-tocopherol, diethylene glycol monoethyl ether, and polysorbate 80.

|  | Claimed Product | |
| --- | --- | --- |
|  | Exzolt. | Claimed |
| TMax.(hrs) | 37.8+_6.4. | 6.3+_1.6 |
| CMax.(ng/ml) | 358.47+_.112.33. | 382.64+_81.37 |
| AUC(ng/ml* day) 0-21 | 1667.56+_.432.61. | 1814.46+_235.74 |
| Egg Residue Max(ug/kg ) | 905 +_.118. | 488+_72 |

Faster onset is seen in Tmax. Lower variability of absorption and lower egg residue are also seen. Use of the complexed fluralaner in a highly water soluble powder formulation by combination with anhydrous polypowder (anhydrous polysorbate 80/hpbcd in, for example, a 1:5 ratio) results in a rapidly absorbed superior product.

The invention claimed is:

1. A method of treating an animal parasitic infection by administering a shelf stable cyclodextrin complex of an isoxazoline wherein the cyclodextrin is 2 hydroxypropyl beta cyclodextrin and the isoxazoline is fluralaner; and
the complex is soluble to less than 20 mg/ml of fluralaner in water.

2. A method of treating an animal parasitic infection using a shelf stable anhydrous pharmaceutical composition, comprising steps of:
combining an isoxazoline cyclodextrin complex maximally soluble to less than 20 mg/ml in water with a polypowder, said polypowder being a polysorbate adsorbed onto 2 hydroxypropyl beta cyclodextrin in an anhydrous form and said polypowder having a shelf life of at least 2 years and a solubility of 20 mg/ml to 30 mg/ml of isoxazoline in water;
combining said isoxazoline cyclodextrin complex and adsorbed polypowder into a dry anhydrous medicament with a shelf life of at least 2 years;
wherein said medicament is administrable with medicinal effect through water or feed orally ingested by an animal.

3. The method of claim 2, wherein said isoxazoline cyclodextrin complex is a fluralaner cyclodextrin complex administered in said water or feed at 0.5 mg of fluralaner per kg of animal body weight wherein said animal is a poultry species.

4. The method of claim 3, wherein said fluralaner cyclodextrin complex is administered twice in a period between 7 to 14 days.

5. The method of claim 2, wherein said isoxazoline complex and polypowder mixture is a fluralaner complex and polypowder mixture administered in hard or soft anhydrous chews at a rate of 2 to 4 mg/kg per month and said animal is a feline or canine.

6. The method of claim 2, wherein the isoxazoline complex and polypowder mixture are combined synergistically with cyclodextrin complexes of macrocyclic lactones increasing solubility and bioavailability and improving taste parameters of said medicaments.

7. The method of claim 6, further comprising a step of combining pyrantel pamoate with said medicament, wherein said combining provides broad spectrum antiparasitic efficiency in an anhydrous shelf stable chewable form.

8. The method of claim 7, wherein said isoxazoline cyclodextrin complex is a fluralaner cyclodextrin complex that has a limited water solubility less than 20 mg/ml.

9. The method of claim 8, wherein said limited water solubility of said fluralaner complex combined with polysorbate polypowder is enhanced from 20 mg/ml to 30 mg/ml of fluralaner in water, inclusive.

10. The method of claim 2, wherein said animal is one of a bovine animal or porcine animal.

11. The method of claim 2, wherein said animal parasitic infestation comprises a tick infestation or lice infestation and the infestation is endoparasitic or ectoparasitic in nature.

12. The method of claim 2, wherein said animal parasitic infestation is a tick infestation of one of a *Dermanyssus* or *Ornithonyssus* species.

13. An orally administrable medicament which treats animal parasitic infections and which is safely ingested by an animal, comprising:
 a polypowder comprising a polysorbate adsorbed onto 2 hydroxypropyl beta cyclodextrin in an anhydrous form having a shelf life of at least 2 years;
 a shelf stable anhydrous pharmaceutical composition comprising a combination of an isoxazoline cyclodextrin complex and polypowder maximally soluble to between 20 mg/ml to 30 mg/ml of isoxazoline inclusive, in water;
 wherein a combination of said isoxazoline cyclodextrin complex with said adsorbed polysorbate forms a dry anhydrous medicament with a shelf life of at least 2 years.

14. The medicament of claim 13, wherein said isoxazoline cyclodextrin complex and polypowder mixture is a fluralaner complex and polypowder mixture optimally treats said animal parasitic infections in hard or soft anhydrous chews at a rate of 2 to 4 mg/kg per month and said animal is a feline or canine.

15. The medicament of claim 13, wherein said isoxazoline cyclodextrin complex and polypowder mixture are combined synergistically with cyclodextrin complexes of macrocyclic lactones increasing solubility and bioavailability and improving taste parameters of said medicaments.

16. The medicament of claim 13, further comprising pyrantel pamoate, wherein said pyrantel pamoate provides a broad spectrum antiparasitic efficiency in an anhydrous shelf stable chewable form.

17. The medicament of claim 13, wherein said isoxazoline is complexed with a cyclodextrin in a stoichiometric ratio of 1:1 or 1:2.

18. The medicament of claim 13, wherein said animal parasitic infestation comprises a tick infestation or lice infestation and the infestation is ectoparasitic in nature.

19. The medicament of claim 15 wherein said infestation comprises a tick infestation or lice infestation or the infestation is endoparasitic or ectoparasitic.

* * * * *